(12) United States Patent
Stanjek et al.

(10) Patent No.: US 8,871,963 B2
(45) Date of Patent: Oct. 28, 2014

(54) PROCESS FOR PREPARING CARBAMATOORGANOSILANES

(75) Inventors: Volker Stanjek, Ampfing (DE); Michael Stepp, Ueberackern (AT)

(73) Assignee: Wacker Chemie AG, Munich (DE)

( * ) Notice: Subject to any disclaimer, the term of this patent is extended or adjusted under 35 U.S.C. 154(b) by 117 days.

(21) Appl. No.: 13/294,674

(22) Filed: Nov. 11, 2011

(65) Prior Publication Data

US 2012/0130103 A1    May 24, 2012

(30) Foreign Application Priority Data

Nov. 23, 2010   (DE) .......................... 10 2010 061 816

(51) Int. Cl.
   *C07F 7/04*    (2006.01)
   *C07F 7/18*    (2006.01)
(52) U.S. Cl.
   CPC .................................. *C07F 7/1892* (2013.01)
   USPC ......................................................... 556/420
(58) Field of Classification Search
   CPC ....................................................... C07F 7/1836
   USPC ......................................................... 556/420
   See application file for complete search history.

(56) References Cited

U.S. PATENT DOCUMENTS

| | | | |
|---|---|---|---|
| 3,494,951 A * | 2/1970 | Berger | .......................... 556/420 |
| 7,060,849 B1 | 6/2006 | Childress et al. | |
| 2002/0016486 A1 | 2/2002 | Pinske | |
| 2003/0088117 A1 | 5/2003 | Hollfelder et al. | |
| 2007/0123644 A1 | 5/2007 | Pfeiffer et al. | |

FOREIGN PATENT DOCUMENTS

| | | |
|---|---|---|
| CN | 1993370 A | 7/2007 |
| DE | 10240388 A1 | 3/2003 |
| EP | 1010704 A2 | 6/2000 |
| EP | 1310501 A1 | 5/2003 |
| JP | 63250391 A | 10/1988 |
| JP | 06025267 A | 2/1994 |
| JP | 200874804 A | 4/2008 |
| WO | 2006012957 A1 | 2/2006 |
| WO | 2007037817 A2 | 4/2007 |
| WO | 2009003956 A2 | 1/2009 |
| WO | WO 2009003956 A2 * | 1/2009 |

OTHER PUBLICATIONS

Maciejewski et al., "Isocyanatopropyltrimethoxysilane—Key Intermediate of New Silane Coupling Agents", Organasilicon Chemistry V, pp. 536-540 (2003).
PatBase abstract in English for DE 10240388 A1, (Sep. 2, 2002).

* cited by examiner

*Primary Examiner* — Fereydoun G Sajjadi
*Assistant Examiner* — Kofi Adzamli
(74) *Attorney, Agent, or Firm* — Caesar, Rivise, Bernstein, Cohen & Pokotilow, Ltd.

(57) ABSTRACT

The invention provides a process for preparing carbamatoorganosilanes (S) of the general formula (7) in which a haloorganosilane (S1) of the general formula (8) is reacted with a metal cyanate (MOCN) and an alcohol (A) of the general formula (9) in the presence of at least one aprotic solvent (L), where $R^1$, $R^3$ and $R^4$ are each an unsubstituted or halogen-substituted hydrocarbyl radical having 1-10 carbon atoms, $R^2$ is a divalent unsubstituted or halogen-substituted hydrocarbyl radical which has 1-10 carbon atoms and may be interrupted by nonadjacent oxygen atoms, X is a halogen atom, and x is a value of 0, 1, 2 or 3, where the removal of the solid metal halides formed as by-products and of any solid metal cyanate residues still present is preceded by distillative removal of at least 50% of the solvent (L).

20 Claims, No Drawings

PROCESS FOR PREPARING CARBAMATOORGANOSILANES

BACKGROUND OF THE INVENTION

The invention relates to a process for preparing carbamatoorganosilanes from corresponding chloroorganosilanes, metal cyanates and alcohols.

The prior art discloses various processes for preparing 3-carbamatopropylsilanes of the formula (1).

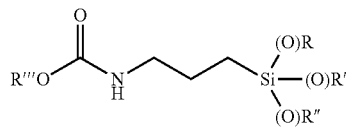
(1)

Common preparation processes usually proceed from 3-aminopropylsilanes of the formula (2). These can be reacted either with dialkyl carbonates or else a mixture of urea and alcohol to give the corresponding carbamatosilanes. The former process variant is described, for example, in WO 2007/037817 and the latter in EP 1010704.

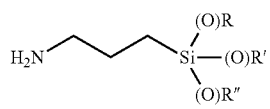
(2)

A disadvantage of this process is the fact that it is necessary to proceed from aminosilanes, which are usually much more expensive than the corresponding 3-chloropropylsilanes of the formula (3).

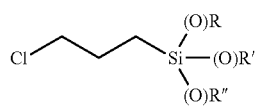
(3)

In addition, only aminoorganosilanes with a propyl spacer between the amino and silyl groups are commercially available, while the corresponding α-aminomethylsilanes of the formula (5) are obtainable only with difficulty and are additionally only of moderate stability. Accordingly, the abovementioned processes are unsuitable for preparation of the α-carbamatomethylsilanes of the formula (4), which are of interest for many (conversion) products. The corresponding α-chloromethylsilanes of the formula (6), in contrast, are preparable without any problem, for example via the photochlorination, described in EP 1310501, of methylchlorosilanes and subsequent alkoxylation, i.e. the exchange of all silicon-bonded chlorine atoms for alkoxy groups.

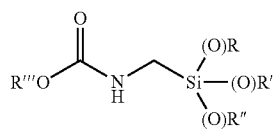
(4)

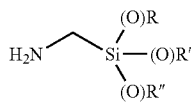
(5)

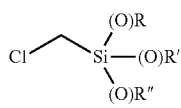
(6)

Thus, a process with which a wide range of different carbamatoorganosilanes is obtainable proceeding from the corresponding chloroorganosilanes would be desirable.

Corresponding processes have likewise already been described, for example in U.S. Pat. No. 3,494,951. Here, a mixture of 3-chloropropylsilanes of the formula (3) is heated with potassium cyanate and an alcohol in a solvent under reflux. The solvent used is preferably dimethylformamide. This forms 3-carbamatopropylsilanes of the formula (1), and potassium chloride as a coproduct. The latter is filtered off and the solvent is removed by distillation.

However, it has been found that this process in accordance with the prior art has numerous distinct shortcomings. Firstly, on account of the comparatively long reaction times and the necessity to use large amounts of solvent, only very poor space-time yields are achieved. In addition, it was found that the removal by filtration of the salt formed as a coproduct is exceptionally problematic since the salt is obtained in such finely crystalline form that the reaction mixture can be filtered only with great difficulty. Finally, it has also been found that the filtered crude product solution also still contains significant amounts of dissolved salt. These then precipitate out under cold conditions (for example when the crude product is stored in unheated rooms in winter) and/or when the solvent is removed, and disrupt the further process steps, for example distillative purification of crude product by means of a thin-film evaporator.

A further process for preparing carbamatoorganosilanes of the formula (1) or (4) from the corresponding chloroorganosilanes (3) or (6) is described in DE 10240388. Here, a suspension of the metal cyanate in a solvent is initially charged and a mixture of methanol and chloroorganosilane is added dropwise. The solvent used is preferably dimethyl sulfoxide or dimethylformamide. Here too, the respective carbamatopropylsilanes form, with potassium chloride as a coproduct. The latter is again removed by filtration, and the solvent is removed by distillation.

However, in this process variant too, various disadvantages were identified. Firstly, relatively large amounts of polymeric and oligomeric by-products are formed. This by-product formation is contradictory to the details in DE 10240388, which describes quantitative yields with product purities of approx. 95%. However, these relatively high molecular weight impurities are not detectable by the gas chromatography analyses, described in DE 10240388, of the reaction mixture, and therefore gas chromatography spectra give correspondingly high purities even when the product solution contains 10-20% oligomers or polymers.

Secondly, in the process described in DE 10240388, the problems of inadequate filterability of the reaction mixture and of the salt burden remaining dissolved in the filtrate are also unsolved.

It was therefore an object of the present invention to develop a process for preparing carbamatoorganosilanes proceeding from chloroorganosilanes which no longer has the disadvantages of the prior art.

DESCRIPTION OF THE INVENTION

The invention provides a process for preparing carbamatoorganosilanes (S) of the general formula (7)

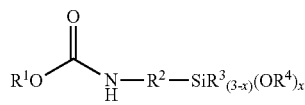
(7)

in which a haloorganosilane (S1) of the general formula (8)

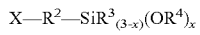
(8)

is reacted with a metal cyanate (MOCN) and an alcohol (A) of the general formula (9)

(9)

in the presence of at least one aprotic solvent (L), where
$R^1$, $R^3$ and $R^4$ are each an unsubstituted or halogen-substituted hydrocarbyl radical having 1-10 carbon atoms,
$R^2$ is a divalent unsubstituted or halogen-substituted hydrocarbyl radical which has 1-10 carbon atoms and may be interrupted by nonadjacent oxygen atoms,
X is a halogen atom, and
x is a value of 0, 1, 2 or 3,
wherein the removal of the solid metal halides formed as by-products and of any solid metal cyanate residues still present is preceded by distillative removal of at least 50% of the solvent (L).

The solids can be removed easily on completion of reaction.

Preferably, the removal, especially filtration, of the metal halides formed as by-products and of any metal cyanates residues still present is preceded by distillative removal of at least 70% and more preferably at least 85% of the solvent (L).

In a particularly preferred variant of the process according to the invention, at least one solvent (L1) having a lower dipole moment than the solvent (L) is added to the reaction mixture before the removal of solids, which is especially effected by filtering off the metal salts. If the solvent (L1) has a higher boiling point than the solvent (L), the solvent (L1) can be added before or after the inventive distillative removal of the solvent (L). However, it is preferable that, irrespective of the particular boiling points of the solvents (L) and (L1), the at least one solvent (L1) is not added until after the distillative removal of the solvent (L).

Preferably at least 0.3 and especially at least 0.5 part by weight and at most 3 and especially at most 1.5 parts by weight of one or more solvents (L1) per part by weight of solvent (L) removed beforehand is/are added to the reaction mixture after the inventive distillative removal of the solvent (L).

After the filtration, the filtercake is preferably washed with the same solvent (L1) which has been added to the reaction mixture after the removal of the solvent (L). Preferably, the filtrates are subsequently combined and the solvent (L1) is removed by distillation.

When the inventive reaction is performed, the different starting materials, reactants, solvents and, if appropriate, also further substances to accelerate the reaction can be initially charged at the start of the reaction, or else not metered in until during the reaction.

The reaction temperature is preferably at least 110° C., particular preference being given to temperatures of at least 120° C. and especially of at least 125° C. The reaction temperature is preferably at most 200° C., especially at most 160° C.

The $R^1$, $R^3$ and $R^4$ radicals may be the same or different. The $R^1$ and $R^4$ radicals are preferably identical, because there may otherwise be exchange of the $R^4$ radicals on the silicon atom. Thus, a mixture of different silanes (S) of the general formula (7) would be obtained in which the individual silane molecules have different $R^1$ and $R^4$ radicals, which is possible but usually undesirable.

The halogen substituents on the $R^1$, $R^2$, $R^3$ and $R^4$ radicals are preferably selected from fluorine and chlorine.

In the silanes (S) or (S1) of the general formula (7) or (8), $R^3$ is preferably a methyl, ethyl, isopropyl or n-propyl radical, particular preference being given to a methyl radical. $R^4$ is preferably a methyl, ethyl, isopropyl or n-propyl radical, particular preference being given to a methyl or ethyl radical. $R^2$ is preferably a propylene or more preferably a methylene radical.

In the silanes (S) of the general formula (7) or the alcohol (A) of the general formula (9), $R^1$ is preferably a methyl, ethyl, isopropyl or n-propyl radical, particular preference being given to a methyl or ethyl radical.

In the silanes (S1) of the general formula (8), X is preferably a chlorine atom.

The silane (S1) may in principle already be present completely in the reaction mixture when the reaction commences. However, in a preferred variant of the process according to the invention, the metered addition of all or at least some, especially at least 80% by weight, of the chloroorganosilane (S1) is not performed until during the reaction.

The advantage of metered addition of the chloroorganosilane (S1) lies in the improvement in the safety of the reaction, since the distinctly exothermic reaction can then be controlled and if necessary even stopped by regulating the metered addition of the silane (S1). Metered addition of the liquid silane (S1) is usually much more convenient than the metered addition of the solid metal cyanate (MOCN), which is likewise conceivable in principle. In contrast, regulation of the exothermicity exclusively via the metered addition of the alcohol (A) is not possible since cyanate (MOCN) and chloroorganosilane (S1) can enter into a distinctly exothermic reaction to form the corresponding isocyanurate (see U.S. Pat. No. 3,494,951) even in the absence of the alcohol (A).

The metal cyanates used may in principle be the cyanates of all mono- or divalent metal ions, preference being given to the alkaline earth metal cyanates and especially the alkali metal cyanates. Particular preference is given to using sodium cyanate and especially potassium cyanate.

Preferably at least 0.8 mol, more preferably at least 0.9 mol and especially at least 1 mol of cyanate ions, and preferably at most 2 mol, more preferably at most 1.5 mol and especially at most 1.2 mol of cyanate ions, are used per mole of silane (S1) of the general formula (8).

The solid metal cyanate (MOCN) is preferably not metered in but instead is initially charged before the reaction commences.

The alcohols (A) used are preferably methanol, ethanol, isopropanol or n-propanol, particular preference being given to methanol and ethanol.

Preferably at least 0.8 mol, more preferably at least 0.9 mol and especially at least 1 mol of alcohol (A), and preferably at most 2 mol, more preferably at most 1.5 mol and especially at most 1.2 mol of alcohol (A), is/are used per mole of silane (S1) of the general formula (8).

The solvent (L) preferably has a boiling point of at least 135° C., more preferably of at least 145° C., and preferably at most 240° C., more preferably at most 220° C., in each case at 0.1 MPa.

The solvents (L) used may be, for example, dimethylformamide, dimethyl sulfoxide, N-methylpyrrolidone, N-methylimidazole, sulfolane, diethylformamide, dimethylacetamide, diethylacetamide, acetylacetone, ethyl acetoacetate, hexamethylphosphoramide, nitriles such as acetonitrile or butyronitrile, and ethers and esters with at least two ether or ester groups per molecule. Preferred solvents (L) are dimethylformamide, dimethyl sulfoxide, N-methylpyrrolidone, sulfolane and diethylformamide, particular preference being given to dimethylformamide.

The solvent is preferably used in amounts such that at least 0.1 and not more than 1.5 part(s) by weight of solvent (L) is/are used per part by weight of total amount of reactant. The total amount of reactant is composed of the amount of silane (S1), metal cyanate (MOCN) and alcohol (A). The solvent is preferably used in amounts such that not more than one part by weight and more preferably 0.7 part by weight of solvent (L) is used per part by weight of total amount of reactant.

The solvent is preferably not metered in but is instead initially charged before the reaction commences.

Optionally, further substances to accelerate the reaction can be used during the reaction. A preferred example is the addition of a metal iodide, preferably of an alkali metal iodide and more preferably of potassium iodide. Equally, it is also possible to add phase transfer catalysts as described, for example, in DE10240388.

Preferably at least 0.01 part by weight, more preferably at least 0.1 part by weight and especially at least 0.5 part by weight of metal iodide, and preferably at most 5 parts by weight, more preferably at most 3 parts by weight and especially at most 2 parts by weight of metal iodide, is/are used per 100 parts by weight of metal cyanate.

The further substances to accelerate the reaction are preferably not metered in but are added before the reaction commences.

The solvent (L1) preferably comprises aromatic and/or aliphatic hydrocarbons (for example the different stereoisomers of pentane, hexane, heptane, octane, etc., cyclopentane, cyclohexane, methylcyclohexane, cycloheptane, etc., benzene, toluene, the different xylene types, etc.), substituted aromatics (e.g. chlorobenzene), heterocyclic aromatics (e.g. pyridine, furan, etc.), ethers (e.g. diethyl ether, methyl t-butyl ether, tetrahydrofuran, dibutyl ether, anisol, etc.), esters (e.g. ethyl acetate, methyl acetate, butyl acetate, alkyl benzoates, dialkyl maleates, dialkyl phthalates, etc.), ketones (e.g. acetone, butanone, etc.) or alcohols (e.g. t-butanol). Particular preference is given to aromatic and/or aliphatic hydrocarbons, for example the different cyclic or noncyclic pentane, hexane, heptane or octane isomers, and toluene or xylene.

The invention is based on the surprising finding that the filterability of the suspension can be distinctly improved by the inventive removal of the solvent (L) and especially by the preferred complete or at least partial exchange of the solvent (L) for a solvent (L1) with a lower dipole moment.

In addition, the inventive removal of the solvent (L) and especially the preferred complete or at least partial exchange of the solvent (L) for a solvent (L1) with a lower dipole moment surprisingly also distinctly reduces the amount of salt remaining in dissolved form in the filtrate.

Particular preference is given to a variant of the process according to the invention in which the total amount of the alcohol (A) to be used is divided in such a way that at least 3% of the total amount of alcohol is initially charged in the reaction mixture before the reaction commences and at least 30% of the total amount of alcohol is not metered into the reaction mixture until during the reaction.

Preferably, the total amount of alcohol (A) to be used is divided in such a way that at least 5% and more preferably at least 8% of the total amount of alcohol is initially charged in the reaction mixture before the reaction commences, and at least 50% and more preferably at least 70% of the total amount of alcohol is not metered in until during the reaction.

Thus, it has been found that, surprisingly, the process according to the invention, in which portions of the alcohol (A) are initially charged and only the remainder is metered in during the reaction, affords much better results than the preparation variants corresponding to the prior art, in which the entire amount of alcohol is either completely initially charged or else completely metered in in the form of a mixture with silane (S1).

DE 10240388 already states that if the alcohol (A) is not metered in until during the reaction, the associated increase in the boiling temperature of the reaction mixture leads to a faster reaction and hence to better space-time yields. What is surprising is, however, that the process variant preferred in accordance with the invention, in which portions of the alcohol (A) are initially charged and only the remainder is metered in during the reaction, when compared to the complete metered addition of the alcohol (A) described in DE 10240388, leads to much better yields and a distinct reduction in formation of oligomeric and/or polymeric impurities.

In a preferred variant of the process according to the invention, the metering rate of the alcohol (A) is controlled via the boiling temperature of the reaction mixture. The alcohol is preferably metered in at such a rate that the reaction mixture over the entire reaction time has a boiling point of >110° C., preferably >120° C. and more preferably >125° C. The upper limit of the boiling point is preferably 150° C. and more preferably 145° C.

An advantageous process is one in which the proportions of haloorganosilane (S1) and alcohol (A) to be metered in are premixed, and this mixture is metered in during the reaction.

If a mixture of silane (S1) and alcohol (A) is metered in, the metering rate of this mixture is preferably controlled via the boiling temperature of the reaction mixture. In this case, the abovementioned preferred limits for the maximum and minimum boiling temperatures preferably apply.

A particular advantage of metered addition of a suitable mixture of silane (S1) and alcohol (A) lies in the fact that excessively rapid metered addition of this mixture, due to the rising proportion of low-boiling alcohol (A) in the reaction mixture, leads to a lowering of the boiling point. A constant boiling point, in contrast, indicates a substantially constant alcohol content in the reaction mixture. Preference is therefore given to a process in which a mixture of silane (S1) and alcohol (A) is metered in and has an alcohol content which indicates any accumulation of unreacted silane (S1) in the reaction mixture associated with excessively rapid metered addition, through a simultaneous accumulation of unreacted alcohol (A) and a resultant fall in boiling point of the reaction mixture. This allows a very rapid reaction regime within an optimal temperature window without any possibility of possibly hazardous accumulation of reactants in the reaction mixture due to any excessively rapid reactant metering. In this way, it is possible to achieve optimal space-time yields.

All above symbols in the above formulae are each defined independently of one another. In all formulae, the silicon atom is tetravalent.

In the examples which follow, unless stated otherwise in any case, all amounts and percentages are based on weight, all pressures are 0.10 MPa (abs.) and all temperatures are 20° C.

Example 1

Inventive Process for Preparing O-methyl N-(3-trimethoxysilylpropyl)carbamate

In a 500 ml four-neck flask with reflux condenser, precision glass stirrer, thermometer, a suspension of 74.46 g of potassium cyanate, 0.73 g of potassium iodide in 117.08 g of dimethylformamide and 3.5 g of methanol is heated to 140° C. Then a solution of 173.7 g of 3-chloropropyltrimethoxysilane and 25.6 g of methanol is metered in under reflux within 2.5 h. The boiling temperature of the reaction mixture remains stable within a temperature range from 130 to 140° C. After addition has ended, stirring is continued for another 2 h, in the course of which the boiling temperature remains within the same temperature range, although initially with a slightly rising trend. Thereafter, the 3-chloropropyltrimethoxysilane reactant is detectable by gas chromatography only in traces of <0.1% based on the amount of product formed.

Thereafter, the mixture is cooled to approx. 50° C. and a total of 106.1 g of dimethylformamide are distilled off at a pressure of approx. 11 mbar. The bottom temperature rises from initially 51° C. up to 100° C., while the top temperature remains substantially constant within a range of 53-56° C. The dimethylformamide distilled off has a purity of >95% and can be reused in a subsequent batch without any problem.

Subsequently, the mixture is cooled to approx. 30° C. Then 100 ml of toluene are added and the mixture is stirred at room temperature for 30 min. Thereafter, all solids are filtered off through a suction filter with a Seitz K900 filter at a pressure of 0.2 bar gauge. The filtration is possible without any problem and is complete within approx. 10 minutes. The filtercake is washed with 70 ml of toluene, which is likewise complete within 5-10 minutes. The filtrates are combined.

In the last step, the toluene is finally removed by distillation at a pressure of approx. 30 mbar and a bottom temperature of 30 to 70° C. This recovers approx. 95% of the amount of toluene used in a purity of >95%. The toluene recovered can be reused without any problem in a subsequent batch.

Toward the end of the distillation, the pressure is lowered to 1 mbar and the bottom temperature is increased to 130° C. for 10 min. The amount of distillate of approx. 17 ml obtained contains essentially the amounts of dimethylformamide and toluene which have remained in the reaction mixture to date and is discarded. The crude product which remains as the distillation bottoms is analyzed by means of $^1$H NMR. The product purity can be determined, for example, by integrating the $CH_3O$—$CO$—$NH$—$CH_2$—$CH_2$—$\underline{CH_2}$—$Si(OCH_3)_3$ signal and comparing this integral value to the signal integrals of an added internal standard such as trimethyl benzenetricarboxylate. The crude product analyzed by this method has a purity of approx. 85%. The crude product is clear. Even in the course of storage at 0° C. for several days, no further solid precipitates out.

Example 2

Inventive Process for Preparing O-methyl N-(3-tri-methoxysilylpropyl)carbamate

The procedure is just as in example 1, except that, after the distillative removal of dimethylformamide, instead of the 100 ml of toluene, an identical amount of xylene is added to the reaction mixture. The filtercake is also not washed with toluene but with 70 ml of xylene. The filtration and the washing of the filtercake likewise proceed without any problem, as described in example 1.

In the last step, the xylene is removed by distillation from the combined filtrates at a pressure of 15-20 mbar and a bottom temperature of 40 to 80° C. This recovers approx. 93% of the amount of xylene used in a purity of >95%. The xylene recovered can be reused without any problem in a subsequent batch.

Toward the end of the distillation, the pressure is lowered to 1 mbar and the bottom temperature is increased to 130° for 10 min. The distillate obtained contains essentially the amounts of dimethylformamide and xylene which have remained in the reaction mixture to date and is discarded.

The crude product obtained has a purity of approx. 84% according to the $^1$H NMR analysis described in example 1. Even in the course of storage at 0° C. for several days, no further solid precipitates out.

Example 3

Inventive Process for Preparing O-methyl N-(3-tri-methoxysilylpropyl)carbamate

The procedure is likewise as in example 1, except that, after the distillative removal of dimethylformamide, instead of the 100 ml of toluene, an identical amount of n-heptane is added to the reaction mixture. The filtercake is also not washed with toluene but with 70 ml of n-heptane. The filtration and the washing of the filtercake, at approx. 15 minutes each, take slightly more time than in the case of use of toluene described in example 1. In spite of this, this entire process step is still performable without any problem.

In the last step, the heptane is removed by distillation from the combined filtrates at a pressure of 30 mbar and a bottom temperature of 40 to 60° C. This recovers approx. 95% of the amount of heptane used in a purity of >95%. The heptane recovered can be reused without any problem in a subsequent batch.

Toward the end of the distillation, the pressure is lowered to 1 mbar and the bottom temperature is increased to 130° for 10 min. The distillate obtained contains essentially the amounts of dimethylformamide and heptane which have remained in the reaction mixture to date and is discarded.

The crude product obtained has a purity of approx. 84% according to the $^1$H NMR analysis described in example 1. Even in the course of storage at 0° C. for several days, no further solid precipitates out.

Comparative Example 1

Noninventive Process for Preparing O-methyl N-(3-tri-methoxysilylpropyl)carbamate The reaction is likewise performed as in example 1. At the end of the reaction, in contrast, the dimethylformamide is not removed, but instead the reaction mixture is filtered directly after cooling.

However, the reaction mixture is barely filterable in practice. In the case of performance of the filtration according to the procedure described in example 1, however, approx. 2.5 h are required for complete filtration. The washing operation for the filtercake with 70 g of dimethylformamide takes a further 1.5-2 h.

Subsequently, the dimethylformamide is distilled off at a pressure of approx. 11 mbar. The bottom temperature rises from initially 51° C. up to 100° C., whereas the top temperature remains substantially constant within a range of 53-56° C. Toward the end of the distillation the pressure is lowered to 1 mbar and the bottom temperature is increased to 130° C. for 10 min.

During the distillation, however, a solid again precipitates out in the distillation bottoms. After cooling to room temperature, it is therefore necessary to filter again.

The resulting crude product has a purity of approx. 83% according to the $^1$H NMR analysis described in example 1. It remains clear at room temperature. In the course of storage at 0° C. for 1 day, however, a solid again precipitates out.

Example 4

Inventive Process for Preparing O-methyl N-(3-tri-methoxysilylpropyl)carbamate

This example describes a procedure which is not preferred, in which the solvent (L) is removed but is not replaced by a solvent (L1) with a lower dipole moment. The implementability of the process is less advantageous than in the case of the preferred procedures of examples 1-3, but still much better than in the case of the noninventive procedure of the comparative example:

The reaction is performed in the same way as in example 1. The DMF is likewise removed by distillation as in example 1. However, no toluene is added before the filtration.

The filtration is performed according to the procedure described in example 1, the filtercake being washed twice with 70 ml of toluene. The filtration and washing operation with a total duration of approx. 1.5 hours is practicable but by no means as unproblematic as in the case of the preferred procedure described in examples 1-3.

In the last step, the toluene is finally removed by distillation at a pressure of approx. 30 mbar and a bottom temperature of 30 to 70° C. This recovers approx. 95% of the amount of toluene used in a purity of >95%. The toluene recovered can be reused without any problem in a subsequent batch.

Toward the end of the distillation, the pressure is lowered to 1 mbar and the bottom temperature is increased to 130° C. for 10 min. The distillate obtained contains essentially the amounts of dimethylformamide and toluene which have remained in the reaction mixture so far and is discarded.

During the distillation, however, a solid again precipitates in the distillation bottoms. After cooling to room temperature, it is therefore necessary to filter again.

The resulting crude product has a purity of approx. 84% according to the $^1$H NMR analysis described in example 1. Even in the course of storage at 0° C. for several days, no further solid precipitates out.

Example 5

Inventive Process for Preparing O-methyl N-(3-tri-methoxysilylpropyl)carbamate

This example describes a procedure which is not preferred, in which the entire amount of the alcohol (A) is not added until during the reaction. The implementability of the process is just as advantageous as in the case of the preferred procedure of examples 1-3. However, a crude product with a somewhat lower product purity is obtained:

The procedure is as in example 1, except that the total amount of methanol to be used is not metered in until during the reaction, in the form of a mixture with 173.7 g of 3-chloropropyltrimethoxysilane.

The resulting crude product has a purity of approx. 73% according to the $^1$H NMR analysis described in example 1. Even in the course of storage at 0° C. for several days, no further solid precipitates out.

Example 6

Inventive Process for Preparing O-methyl N-(methyldimethoxysilylmethyl)carbamate The procedure is as in example 1, except that what is metered into the reaction mixture is not a solution of 135.2 g of 3-chloropropyltrimethoxysilane and 25.6 g of methanol but instead a solution of 173.7 g of chloromethylmethyldimethoxysilane and 25.6 g of methanol.

The resulting crude product is analyzed by means of $^1$H NMR analysis similarly to the procedure described in example 1, except that the integral of the CH$_3$O—CO—NH—<u>CH$_2$</u>—Si(CH$_3$)(OCH$_3$)$_2$ signal is used for the determination of the product purity. The result is a purity of approx. 79%.

Even in the course of storage of the crude product at 0° C. for several days, no further solid precipitates out.

The invention claimed is:

1. A process for preparing carbamatoorganosilanes (S) of the general formula (7)

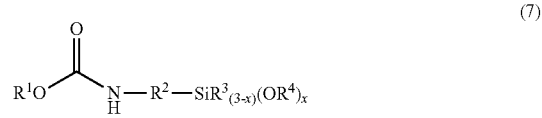

in which a haloorganosilane (S1) of the general formula (8)

is reacted in a reaction mixture with a metal cyanate (MOCN) and an alcohol (A) of the general formula (9)

in the presence of at least one aprotic solvent (L), where R$^1$, R$^3$ and R$^4$ are each an unsubstituted or halogen-substituted hydrocarbyl radical having 1-10 carbon atoms,
R$^2$ is a divalent unsubstituted or halogen-substituted hydrocarbyl radical which has 1-10 carbon atoms and is optionally interrupted by nonadjacent oxygen atoms,
X is a halogen atom, and
x is a value of 0, 1, 2 or 3,
wherein removal of the solid metal halides formed as by-products and of any solid metal cyanate residues still present is preceded by distillative removal of at least 50% of the solvent (L).

2. The process as claimed in claim 1, in which at least one solvent (L1) having a lower dipole moment than the solvent (L) is added to the reaction mixture before the removal of solids.

3. The process as claimed in claim 1, in which the reaction temperature is 110° C. to 200° C.

4. The process as claimed in claim 1, in which R$^3$ is selected from the group consisting of methyl, ethyl, isopropyl and n-propyl radical.

5. The process as claimed in claim 1, in which $R^4$ is selected from the group consisting of methyl, ethyl, isopropyl and n-propyl radical.

6. The process as claimed in claim 1, in which $R^2$ is a propylene or methylene radical.

7. The process as claimed in claim 1, in which $R^1$ is selected from the group consisting of methyl, ethyl, isopropyl and n-propyl radical.

8. The process as claimed in claim 1, in which X is a chlorine atom.

9. The process as claimed in claim 1, in which the solvent (L) is selected from the group consisting of dimethylformamide, dimethyl sulfoxide, N-methylpyrrolidone, N-methylimidazole, sulfolane, diethylformamide, dimethylacetamide, diethylacetamide, acetylacetone, ethyl acetoacetate, hexamethylphosphoramide, acetonitrile, butyronitrile, and ethers and esters with at least two ether or ester groups per molecule.

10. The process as claimed in claim 2, in which the solvent (L1) is selected from the group consisting of aromatic and aliphatic hydrocarbons, substituted aromatics, heterocyclic aromatics, ethers, esters and ketones.

11. The process as claimed in claim 1, in which a total amount of the alcohol (A) of the general formula (9) to be used is divided in such a way that at least 3% of the total amount of alcohol is initially charged in the reaction mixture before the reaction commences and at least 30% of the total amount of alcohol is not metered into the reaction mixture until during the reaction.

12. The process as claimed in claim 2, in which the reaction temperature is 110° C. to 200° C.

13. The process as claimed in claim 12, in which $R^3$ is selected from the group consisting of methyl, ethyl, isopropyl and n-propyl radical.

14. The process as claimed in claim 13, in which $R^4$ is selected from the group consisting of methyl, ethyl, isopropyl and n-propyl radical.

15. The process as claimed in claim 14, in which $R^2$ is a propylene or methylene radical.

16. The process as claimed in claim 15, in which $R^1$ is selected from the group consisting of methyl, ethyl, isopropyl and n-propyl radical.

17. The process as claimed in claim 16, in which X is a chlorine atom.

18. The process as claimed in claim 17, in which the solvent (L) is selected from the group consisting of dimethylformamide, dimethyl sulfoxide, N-methylpyrrolidone, N-methylimidazole, sulfolane, diethylformamide, dimethylacetamide, diethylacetamide, acetylacetone, ethyl acetoacetate, hexamethylphosphoramide, acetonitrile, butyronitrile, and ethers and esters with at least two ether or ester groups per molecule.

19. The process as claimed in claim 18, in which the solvent (L1) is selected from the group consisting of aromatic and aliphatic hydrocarbons, substituted aromatics, heterocyclic aromatics, ethers, esters and ketones.

20. The process as claimed in claim 19, in which a total amount of the alcohol (A) of the general formula (9) to be used is divided in such a way that at least 3% of the total amount of alcohol is initially charged in the reaction mixture before the reaction commences and at least 30% of the total amount of alcohol is not metered into the reaction mixture until during the reaction.

* * * * *